United States Patent

Sasaki et al.

Patent Number: 5,128,398
Date of Patent: Jul. 7, 1992

[54] PHENOLIC COMPOUND AND ITS USE AS STABILIZER FOR BUTADIENE POLYMER

[75] Inventors: Manji Sasaki, Nishinomiya; Shinichi Yachigo, Toyonaka; Kikumitsu Inoue, Nishinomiya; Shinya Tanaka, Toyonaka; Takeshi Takata, Nishinomiya; Kanako Ida, Ashiya, all of Japan

[73] Assignee: Sumitomo Chemical Company, Limited, Osaka, Japan

[21] Appl. No.: 478,474

[22] Filed: Feb. 12, 1990

Related U.S. Application Data

[63] Continuation-in-part of Ser. No. 286,873, Dec. 20, 1988, abandoned.

[30] Foreign Application Priority Data

Dec. 23, 1987 [JP] Japan .................. 62-327731
Apr. 13, 1989 [JP] Japan .................. 1-94937

[51] Int. Cl.⁵ .................. C08K 5/13; C07C 69/54
[52] U.S. Cl. .................. 524/291; 252/404; 524/100; 524/302; 524/151; 560/140
[58] Field of Search .................. 524/291; 560/140

[56] References Cited

U.S. PATENT DOCUMENTS

| | | | |
|---|---|---|---|
| 3,984,372 | 10/1976 | Cottman | 560/140 |
| 4,168,387 | 9/1979 | Cottman | 560/104 |
| 4,365,032 | 12/1982 | Yosizato et al. | 524/99 |
| 4,525,514 | 6/1985 | Yachigo et al. | 524/291 |
| 4,562,281 | 12/1985 | Takahashi et al. | 560/140 |
| 4,732,923 | 3/1988 | Takata et al. | 524/291 |
| 4,774,274 | 9/1988 | Takata et al. | 524/291 |
| 5,045,581 | 8/1991 | Takata et al. | 524/291 |
| 5,047,461 | 9/1991 | Takata et al. | 524/291 |

FOREIGN PATENT DOCUMENTS 243956 11/1987 European Pat. Off. .
61-47723 3/1986 Japan .
62-223248 10/1987 Japan .

*Primary Examiner*—Veronica P. Hoke
*Attorney, Agent, or Firm*—Stevens, Davis, Miller & Mosher

[57] ABSTRACT

A compound represented by the formula of:

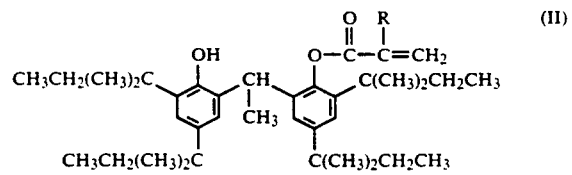

wherein R is hydrogen or methyl. This compound is useful as a stabilizer for butadiene polymers.

20 Claims, No Drawings

PHENOLIC COMPOUND AND ITS USE AS STABILIZER FOR BUTADIENE POLYMER

This is a Continuation-In-Part application of Ser. No. 07/286,873 filed on Dec. 20, 1988 now abandoned.

The present invention relates to a phenolic compound having good solubility in solvents, and its use as a stabilizer for butadiene polymers.

Butadiene polymers such as solution polymerized polybutadiene rubber (BR), solution polymerized styrene-butadiene copolymer rubber (SBR) and styrene-butadiene block copolymer (SBS) are generally produced by anionic polymerization in a hydrocarbon solvent using an organolithium compound as a catalyst or using a Ziegler catalyst. Removal of the solvent from a polymer solution after completion of the polymerization has hitherto been performed by a steam-stripping method, but recently, a method of directly removing the solvent which can theoretically minimize the amount of steam required has been proposed for saving of energy.

However, the latter process is normally carried out at a high temperature of about 150°–200° C. which is considerably higher than the boiling point of the polymerization solvents. Therefore, this method suffers from problems such as gel formation and discoloration of polymers after the high temperature process. Such being the case, it is desirable to improve the resistance to thermal degradation and discoloration in the preparation of butadiene polymers, especially in the absence of oxygen.

Furthermore, in the extrusion molding or injection molding of SBS or high-impact polystyrenes modified with BR, SBR or SBS, high temperature and high speed processing are required, and owing to insufficient thermal resistance, fish eye gel often occurs, causing problems such as deterioration of film properties and discoloration of the film. Thus, a solution of these problems has been earnestly demanded.

It has been well known to use various antioxidants of the phenol type, phosphorus type and sulfur type during the preparation and processing of butadiene polymers. For example, phenolic antioxidants such as 2,6-di-t-butyl-4-methylphenol, 2,2′-methylenebis(6-t-butyl-4-methylphenol), n-octadecyl 3-(3,5-di-t-butyl-4-hydroxyphenyl)propionate, triethylene glycol bis[3-(3-t-butyl-4-hydroxy-5-methylphenyl)propionate], pentaerythrityl tetrakis[3-(3,5-di-t-butyl-4-hydroxyphenyl)propionate] and 1,3,5-trimethyl-2,4,6-tris(3,5-di-t-butyl-4-hydroxybenzyl)benzene are used alone or in combination with phosphorus type antioxidants such as tris(nonylphenyl) phosphite and distearyl pentaerythrityl diphosphite or in combination with sulfur type antioxidants such as dilauryl thiodipropionate, dimyristyl thiodipropionate, distearyl thiodipropionate and pentaerythrityl tetrakis(3-laurylthiopropionate).

However, these methods are not sufficient to prevent the thermal deterioration (gelation) which may occur, especially in the absence of oxygen, in a high temperature process for the separation of the polymer from a polymer solution, in the preparation of butadiene polymers or in high temperature processing of butadiene polymers.

Further, a phenolic compound represented by the following formula (I) has been known as a stabilizer for butadiene polymers.

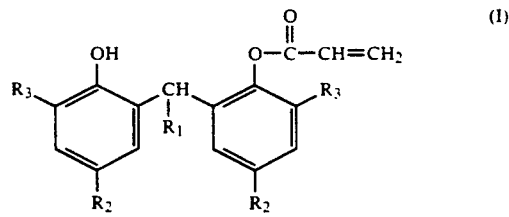

For example, U.S. Pat. No. 4,525,514 discloses a compound of the above formula (I) where $R_1$ is hydrogen, $R_2$ is an alkyl of 1–4 carbon atoms and $R_3$ is t-butyl. It mentions that in particular, the compound where $R_2$ is methyl, namely, 2-t-butyl-6-(3-t-butyl-2-hydroxy-5-methylbenzyl)-4-methylphenyl acrylate is effective as a stabilizer for butadiene polymers. This stabilizer prevents thermal deterioration (gelation), especially in the absence of oxygen, in a high temperature process for separation of the polymer from a polymer solution, in the preparation of butadiene polymers or in high temperature processing of butadiene polymers, but it has become apparent that the use of this stabilizer has the problem that the separated polymer is practically insufficient in its hue.

U.S. Pat. No. 4,774,274 discloses a compound of the above formula (I) where $R_1$ is an alkyl having 1–4 carbon atoms, $R_2$ is a group linking through a quaternary carbon atom (such as t-butyl) or is phenyl and $R_3$ is t-butyl, to be effective for preventing the butadiene polymer from thermal deterioration (gelation) and discoloration in the absence of oxygen.

On the other hand, as an antioxidant for various synthetic resins for preventing discoloration caused by the oxidative deterioration in the presence of oxygen, U.S. Pat. No. 4,365,032 proposed a monoester compound of 2,2′-alkylidenebis(4,6-di-alkyl substituted phenol), including the acrylate represented by the above mentioned formula (I). This patent specifies $R_1$ in the formula (I) to be hydrogen or an alkyl of 1–10 carbon atoms and $R_2$ and $R_3$ to be an alkyl of 1–4 carbon atoms, a cycloalkyl of 5–6 carbon atoms or a methylsubstituted cycloalkyl of 5–6 carbon atoms. However, this patent makes no mention of preventing the discoloration or thermal deterioration (gelation) which may occur, especially in the absence of oxygen, in a high temperature process for separating a polymer from a polymer solution in the production of butadiene polymers or in high temperature processing of butadiene polymers. Besides, the compounds specifically exemplified in the patent showed no sufficient effect in preventing thermal deterioration or discoloration, especially in the absence of oxygen, in a high temperature process in the production of butadiene polymers or in high temperature processing of butadiene polymers.

Furthermore, Japanese Pat. Kokai No. 62-223248 discloses stabilizing polyethylene by the combined use of the phenolic compound of the formula (I) with other phenolic compound and/or a phosphorus-containing compound. This patent publication merely mentions the stabilization of polyethylene and does not teach stabilizing butadiene polymers, especially to prevent the thermal deterioration (gelation) or discoloration in the absence of oxygen.

In general, when a stabilizer is added in the production of butadiene polymers, it is dissolved in a hydrocarbon solvent which is otherwise used as a polymerization solvent, and the solution is added to a polymer solution after the termination of the polymerization reaction. Thus, the stabilizer should desirably have high solubility in the hydrocarbon solvents. Low solubility often causes clogging in piping because the stabilizer solution becomes a slurry, requiring a large investment to avoid the clogging. The known stabilizers, particularly, the compounds exhibiting good effects to prevent the butadiene polymers from thermal deterioration (gelation) and discoloration in the absence of oxygen at a high temperature in the production or processing of the polymers, do not have high solubility in the hydrocarbon solvents.

Further, when the polymer products containing additives are used for a long period, there are cases where the additives come out on the surface of the polymer. Such phenomenon is known as "blooming" or "bleeding." If the blooming or bleeding occurs, the product gets cloudy and loses its transparency, resulting in a lowered commercial value. Therefore, stabilizers for polymers are, of course, desirable to be stable in the polymer, i.e., not causing such blooming or bleeding.

An object of the present invention is to provide a compound which can prevent thermal deterioration (gelation) or discoloration of butadiene polymers, especially in the absence of oxygen, at a high temperature process for separating a polymer from a polymer solution in the production of butadiene polymers or at high temperature processing of butadiene polymers.

Another object of the present invention is to provide a compound having good solubility in the hydrocarbon solvents used in the production of butadiene polymers.

A further object of the present invention is to provide a compound stable in the butadiene polymers, i.e., not causing the blooming or bleeding.

Another further object of the present invention is to stabilize butadiene polymers using such compound.

As a result of the inventors' research, they have found that a phenolic compound of a specific structure satisfies the above objects, that is, such compound has good solubility in hydrocarbon solvents and hence, can be easily added in the production of butadiene polymers. Further, butadiene polymers containing this compound are stable against thermal deterioration (gelation) or discoloration in the absence of oxygen at a high temperature process in the production thereof and at high temperature processing of the polymers, and they hardly cause blooming or bleeding. The present invention has been accomplished based on these findings.

Thus, the present invention provides a phenolic compound represented by the formula (II):

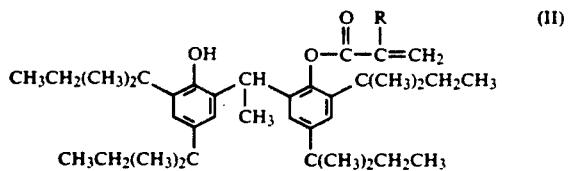

wherein R is hydrogen or methyl.

The present invention also concerns a stabilizer for butadiene polymers comprising the compound of the formula (II), a method for stabilizing butadiene polymers by incorporating the compound of the formula (II), and a butadiene polymer composition containing the compound of the formula (II).

The phenolic compound represented by the formula (II) is included in the genus of the formula (I) or close to the phenolic compounds disclosed in the above mentioned prior publications, but specifically has never been known. According to the present invention, it has been found that a specific compound, namely the compound of the formula (II) among the phenolic compounds of the formula (I), has conspicuously superior properties to the known compounds.

The substituent $R_1$ in the phenolic compounds of the formula (I) is preferably as small as possible in carbon number of alkyl for preventing gelation of butadiene polymers at a high temperature, and methyl is most preferred. For $R_2$, a group represented by $-C(CH_3)_2-R'$ containing a quaternary carbon atom is preferred for preventing discoloration of butadiene polymers, and especially preferred are t-butyl, t-amyl and t-octyl. As $R_3$, preferred is a group represented by $-C(CH_3)_2-R'$ containing a quaternary carbon atom for preventing gelation of butadiene polymers at a high temperature, and especially preferred are t-butyl and t-amyl. Thus, the phenolic compound of the present invention represented by the formula (II) is effective to prevent the gelation and discoloration of butadiene polymers at a high temperature.

Further, the important characteristic of the phenolic compound (II) according to the present invention is its peculiarly high solubility in hydrocarbon solvents as compared with the known similar compounds.

Furthermore, the phenolic compound (II) is stable in the butadiene polymers and does not cause blooming or bleeding, even when the polymers containing the compound are used for long periods of time. Accordingly, the phenolic compound (II) exhibits good effects that it is excellent in preventing butadiene polymers from gelation and discoloration at a high temperature in the absence of oxygen, that it is stable in the butadiene polymers against long period usage, and further, that it has high solubility in hydrocarbon solvents.

The phenolic compound of the formula (II) of the present invention can be produced by an esterification reaction of 2,2'-ethylidenebis(4,6-di-t-amylphenol) with acrylic or methacrylic acid or their derivatives such as acryloyl or methacryloyl chloride, acryloyl or methacryloyl bromide and acrylic or methacrylic anhydride (see U.S. Pat. Nos. 4,525,514, 4,562,281 and 4,365,032).

When the phenolic compound of the formula (II) is used as a stabilizer for butadiene polymers, such butadiene polymers include, for example, solution polymerized polybutadiene rubber (BR), solution polymerized styrene-butadiene copolymer rubber (SBR), styrene-butadiene block copolymer (SBS) and high-impact polystyrenes (HI-PS) modified with BR, SBR or SBS. These may be used alone or in combination with other polymers.

The amount of the phenolic compound to be incorporated into the butadiene polymer is 0.05-2 parts by weight, preferably 0.1-1 part by weight per 100 parts by weight of the butadiene polymer. When the amount of the phenolic compound is less than 0.05 part by weight, the desired effect is insufficient, and even it exceeds 2 parts by weight, the corresponding effect cannot be exhibited and this is not economical.

When the phenolic compound of the present invention is added to butadiene polymers, the compound is dissolved in hydrocarbon solvents used as polymerization solvents for butadiene polymers, and the solution is added to the polymerized reaction solution of a butadiene polymer after termination of anionic polymerization reaction. Alternatively, the phenolic compound may be added to the polymer by dry blending at the time of processing, such as extrusion molding, injection molding and the like.

According to the present invention, a butadiene polymer composition having excellent properties can be obtained by incorporating the above mentioned phenolic compound as a stabilizer into a butadiene polymer and, if necessary, there may further be added other phenolic compounds and/or other additives such as ultraviolet absorbers, light stabilizers, antioxidants, metal deactivators, metallic soaps, nucleating agents, lubricants, antistatic agents, fire retardants, pigments and fillers.

Examples of these additives are as follows. Phenolic antioxidants:

2,6-Di-t-butyl-4-methylphenol,
n-Octadecyl 3-(3,5-di-t-butyl-4-hydroxyphenyl)propionate,
Triethylene glycol bis[3-(3-t-butyl-4-hydroxy-5-methylphenyl)propionate],
Pentaerythrityl tetrakis[3-(3,5-di-t-butyl-4-hydroxyphenyl)propionate,
1,3,5-Trimethyl-2,4,6-tris(3,5-di-t-butyl-4-hydroxybenzyl)benzene,
3,9-Bis{2-[3-(3-t-butyl-4-hydroxy-5-methylphenyl)propionyloxy]-1,1-dimethylethyl}-2,4,8,10-tetraoxaspiro[5.5]undecane.

Ultraviolet absorbers:

2-Hydroxy-4-methoxybenzophenone,
2-Hydroxy-4-n-octoxybenzophenone,
2-(2-Hydroxy-5-methylphenyl)benzotriazole,
2-(3-t-butyl-2-hydroxy-5-methylphenyl)-5-chlorobenzotriazole,
2-(3,5-Di-t-butyl-2-hydroxyphenyl)-5-chlorobenzotriazole,
2-(3,5-Di-t-amyl-2-hydroxyphenyl)benzotriazole,
2,4-Di-t-butylphenyl 3,5-di-t-butyl-4-hydroxybenzoate,
[2,2'-Thiobis(4-t-octylphenolate)]/n-butylamine Ni salt.

Hindered amine light stabilizers:

2,2,6,6-Tetramethyl-4-piperidyl benzoate,
Bis(2,2,6,6-tetramethyl-4-piperidyl) sebacate,
Bis(1,2,2,6,6-pentamethyl-4-piperidyl) 2-(3,5-di-t-butyl-4-hydroxybenzyl)-2-n-butylmalonate,
4-[3-(3,5-Di-t-butyl-4-hydroxyphenyl)propionyloxy]-1-[2-{3-(3,5-di-t-butyl-4-hydroxyphenyl)propionyloxy}-ethyl]-2,2,6,6-tetramethylpiperidine,
Polycondensate of dimethyl succinate and 4-hydroxy-1-(2-hydroxyethyl)-2,2,6,6-tetramethylpiperidine,
Poly{[6-(1,1,3,3-tetramethylbutyl)amino-1,3,5-triazine2,4-diyl][(2,2,6,6-tetramethyl-4-piperidyl)-imino]hexamethylene[(2,2,6,6-tetramethyl-4-piperidyl)imino]},
Poly{[6-morpholino-1,3,5-triazine-2,4-diyl][(2,2,6,6-tetramethyl-4-piperidyl)imino]hexamethylene[(2,2,6,6-tetramethyl-4-piperidyl)imino]},
2-Methyl-2-(2,2,6,6-tetramethyl-4-piperidyl)amino-N-(2,2,6,6-tetramethyl-4-piperidyl)propionamide.

Sulfur-containing antioxidants:

Dilauryl thiodipropionate,
Dimyristyl thiodipropionate,
Distearyl thiodipropionate,
Pentaerythrityl tetrakis(3-dodecylthiopropionate), 3,9-bis(2-dodecylthioethyl)-2,4,8,10-tetraoxaspiro[5.5]undecane.

Phosphorus-containing antioxidants:

Distearyl pentaerythrityl diphosphite,
Tris(2,4-di-t-butylphenyl) phosphite,
Tris(2-t-butyl-4-methylphenyl) phosphite,
Bis(2,4-di-t-butylphenyl) pentaerythrityl diphosphite,
Tetrakis(2,4-di-t-butylphenyl) 4,4'-biphenylene diphosphonite,
Bis(2,6-di-t-butyl-4-methylphenyl) pentaerythrityl diphosphite.

A stabilizer for butadiene polymers which contains the phenolic compound of the formula (II) as an active ingredient may comprise this compound alone or may comprise a mixture of the compound with a carrier which does not affect the properties of the butadiene polymers or may further comprise a mixture of the compound with at least on of the above mentioned additives. Further, it may, of course, comprise a solution of the compound in a hydrocarbon solvent as mentioned above.

The phenolic compound as specified in the present invention is effective, when incorporated into butadiene polymers, to prevent gelation and discoloration caused by thermal deterioration especially in the absence of oxygen. Accordingly, a butadiene polymer free from gelation and discoloration can be stably obtained when the polymer is separated from a polymer solution at a high temperature after the termination of the polymerization reaction. Furthermore, butadiene polymers containing the phenolic compound are also stable against thermal deterioration during processing steps such as injection molding and extrusion molding. For example, formation of fish eye gel at a film forming step or formation of microgel which may cause reduction of gloss or reduction of transparency at an injection molding step can be prevented to give products of high quality, free from discoloration. The butadiene polymers containing the phenolic compound are further inhibited in the blooming or bleeding of the compound, and transparency of the polymers is maintained for a long time.

In addition, the phenolic compound of the present invention has very high solubility in hydrocarbon solvents and hence, can be added easily to a butadiene polymer solution after the termination of polymerization reaction as a solution in a solvent. Thus, operability is very good, and conventionally used apparatuses for production can be used without any modification.

The present invention will be explained in more detail with reference to the following examples, but the present invention should never be limited to these examples. In the examples, the following compounds AO-1 to AO-4 were used for comparison.

AO-1: 2-t-Butyl-6-(3-t-butyl-2-hydroxy-5-methylbenzyl)-4-methylphenyl acrylate
AO-2: 2,4-Di-t-butyl-6-[1-(3,5-di-t-butyl-2-hydroxyphenyl)ethyl]phenyl acrylate
AO-3: 2,6-Di-t-butyl-4-methylphenol
AO-4: n-Octadecyl 3-(3,5-di-t-butyl-4-hydroxyphenyl)propionate

EXAMPLE 1

Preparation of 2,4-di-t-amyl-6-[1-(3,5-di-t-amyl-2-hydroxyphenyl)ethyl]phenyl acrylate (hereinafter referred to as II-1)

In a 2 liter four-necked flask equipped with a thermometer, a stirrer, a condenser and a dropping funnel were charged 494.8 g (1.0 mol) of 2,2'-ethylidenebis(4,6-di-t-amylphenol), 72.1 g (1.0 mol) of acrylic acid, 400 g of n-heptane and 212.5 g (2.1 mol) of triethylamine. Under a nitrogen atmosphere, 107.3 g (0.7 mol) of phosphorus oxychloride was added dropwise with stirring. After completion of the addition, the flask was kept at 80° C. for 1 hour, and then 500 g of water was added and stirred with the reaction mixture at 60° C., followed by separation into layers.

The separated oil layer was repeatedly washed with water until the aqueous layer became nearly neutral, and then the oil layer was cooled to 5° C. with stirring to precipitate crystals. Stirring was further continued at the same temperature for sufficient precipitation. The crystals were collected by filtration, washed with cold n-heptane and dried under reduced pressure to obtain 210.7 g of white crystalline 2,4-di-t-amyl-6-[1-(3,5-di-t-amyl-2-hydroxyphenyl)ethyl]phenyl acrylate (II-1). m.p. 120°-121.5° C.

| Elemental Analysis: | Found | (Calcd.) |
|---|---|---|
| C: | 80.94% | (80.98%) |
| H: | 10.26% | (10.28%) |
| Mass Analysis (FD-MS): | M/Z 548 (M⁺) | |

EXAMPLE 2

Preparation of 2,4-di-t-amyl-6-[1-
-(3,5-di-t-amyl-2-hydroxyphenyl)ethyl]phenyl
methacrylate (hereinafter referred to as II-2)

In a 2 liter four-necked flask equipped with a thermometer, a stirrer, a condensor and a dropping funnel were charged 494.8 g (1.0 mol) of 2,2'-ethylidenebis(4,6-di-t-amylphenol), 86.1 g (1.0 mol) of methacrylic acid, 400 g of n-heptane and 212.5 g (2.1 mol) of triethylamine. Under a nitrogen atmosphere, 107.3 g (0.7 mol) of phosphorus oxychloride was added dropwise with stirring. After completion of the addition, the flask was kept at 80° C. for 1 hour, and then 500 g of water was added and stirred with the reaction mixture at 60° C. followed by separation into layers.

The separated oil layer was repeatedly washed with water until the aqueous layer became nearly neutral, and then the oil layer was cooled to 5° C. with stirring to precipitate crystals. Stirring was further continued at the same temperature for sufficient precipitation. The crystals were collected by filtration, washed with cold n-heptane and dried under reduced pressure to obtain 268.6 g of white crystalline 2,4-di-t-amyl-6-[1-(3,5-di-t-amyl-2-hydroxyphenyl)ethyl]phenyl methacrylate (II-2). m.p. 103°-105° C.

| Elemental Analysis: | Found | (Calcd.) |
|---|---|---|
| C: | 81.14% | (81.09%) |
| H: | 10.43% | (10.39%) |
| Mass Analysis (FD-MS): | M/Z 562 (M⁺) | |

EXAMPLE 3

Solubility in hydrocarbon solvents was examined for the compounds II-1 and II-2 of the present invention and for the compounds AO-1 and AO-2 which are structurally similar to the compounds of the present invention. The hydrocarbon solvents used were n-hexane and cyclohexane. The results are shown in Table 1.

TABLE 1

| | Solubility at 20° C. (g/100 g solvent) | |
|---|---|---|
| Solvent/Compound* | n-Hexane | Cyclohexane |
| II-1 | 55 | 89 |
| II-2 | 65 | 108 |
| AO-1 | 1.5 | 4.0 |
| AO-2 | 1.1 | 2.4 |

*AO-1: Compound of the formula (I) where $R_1$ = H, $R_2$ = $CH_3$, $R_3$ = $C(CH_3)_3$.
AO-2: Compound of the formula (I) where $R_1$ = $CH_3$, $R_2$ = $R_3$ = $C(CH_3)_3$.

EXAMPLE 4

Polymerization of 1,3-butadiene was effected at 60°-65° C. using n-butyl lithium as a catalyst in n-hexane under a nitrogen atmosphere. After termination of the polymerization with isopropyl alcohol as a terminator, a n-hexane solution of 2,4-di-t-amyl-6-[1-(3,5-di-t-amyl-2-hydroxyphenyl)ethyl]phenyl acrylate (II-1) was added thereto and then, n-hexane was removed by flash distillation at 190°-200° C. under the nitrogen atmosphere to obtain a polybutadiene rubber composition (BR). Alternatively, the procedure was repeated using 2,4-di-t-amyl-6-[1-(3,5-di-t-amyl-2-hydroxyphenyl)ethyl]phenyl methacrylate (II-2) in place of the acrylate II-1. The loading amount of the compound II-1 or II-2 is shown in Table 2 with a unit of part by weight per 100 parts by weight of the polybutadiene.

The resulting polybutadiene rubber composition was subjected to a kneading test under the following conditions in a nitrogen stream using Laboplastmill (model 40-100 manufactured by Toyo Seiki Co.). The gelation preventing effect at the kneading was evaluated with torque behavior contingent to gelation. The results are shown in Table 2. The effect to prevent the gelation is shown by a gelation time required to reach a peak value of the torque and the longer time means a higher effect to prevent the gelation.

| (1) Mixer | Model R-60 |
|---|---|
| (2) Range of torque measured | 0–500 kg-cm |
| (3) Amount of charged composition | 30 g |
| (4) Flow rate of nitrogen gas | 1 l/min |
| (5) Test temperature | 180° C. |
| (6) Revolution | 10 rpm during preheating for 3 min; thereafter 60 rpm. |

Furthermore, the degree of discoloration of the polybutadiene rubber after the high temperature process for the preparation thereof was evaluated by the naked eye and shown in Table 2 by the following criteria.

○: No discoloration
Δ: Discoloration in light yellow
X : Discoloration in yellow

COMPARATIVE EXAMPLE 1

Experiments were effected in the same manner as in the above Example 4 except that compounds AO-1, AO-2, AO-3 and AO-4 were used in place of the compound II-1 or II-2, and the preventive effect of the test compounds against gelation and discoloration of the polybutadiene rubber were evaluated. The results and loading amount of the test compounds are shown in Table 2.

TABLE 2

| Test Compound | | Example 4 | | | | Comparative Example 1 | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Loading amount | II-1 | 0.2 | 0.4 | | | | | | | | | | | None |
| | II-2 | | | 0.2 | 0.4 | | | | | | | | | |
| | AO-1 | | | | | 0.4 | 0.8 | | | | | | | |
| | AO-2 | | | | | | | 0.2 | 0.4 | | | | | |
| | AO-3 | | | | | | | | | 0.4 | 0.8 | | | |
| | AO-4 | | | | | | | | | | | 0.4 | 0.8 | |
| Gelation time (min.) | | 47 | 71 | 43 | 68 | 31 | 42 | 45 | 67 | 10 | 14 | 8 | 13 | 5 |
| Degree of discoloration | | O | O | O | O | Δ | X | O | O | O | Δ | O | O | X |

EXAMPLE 5

Under a nitrogen atmosphere, 0.8 parts by weight of n-butyl lithium was added to a cyclohexane solution containing 20 parts by weight of 1,3-butadiene, and the reaction was allowed to proceed at 70° C. for 1 hour. Thereafter, to the reaction product were added in sequence 20 parts by weight of styrene, 15 parts by weight of 1,3-butadiene and 45 parts by weight of styrene, and polymerization was effected at 70° C. for 1 hour, respectively. After termination of the polymerization, to the reaction product was added a cyclohexane solution of 2,4-di-t-amyl-6-[1-(3,5-di-t-amyl-2-hydroxyphenyl)ethyl]phenyl acrylate (II-1), and cyclohexane was removed by heating under the nitrogen atmosphere to obtain a block copolymer composition of B-A-B-A structure containing 35% by weight of butadiene. Alternatively, the procedure was repeated using 2,4-di-t-amyl-6-[1-(3,5-di-t-amyl-2-hydroxyphenyl)ethyl]phenyl methacrylate (Ii-2) in place of the acrylate II-1. The loading amount of the test compound is shown in Table 3 with a unit of part by weight per 100 parts by weight of the block copolymer.

The resulting block copolymer compositions were subjected to a strand fall extrusion test under the following conditions using Laboplastmill extruder, and the evaluation was conducted by measuring gel content in the stranded product as a toluene-insoluble fraction. The gel content was determined by dipping about 1 g of the accurately weighed stranded product sample in 200 ml of toluene, stirring it for 24 hours, then collecting it by filtration using a 200 mesh wire gauze, drying the unfiltered matter, weighing it as the gel and calculating the gel content from the weight. The results are shown in Table 3.

(1 Test Condition: Testing machine: Laboplastmill Model 40-100 (Toyo Seiki Co.)
(2) Extruder: Model D20-25 (Toyo Seiki Co.)
(3) Diameter of strand die: 0.5 mm φ
(4) Cylinder temperature: 230°-260° C.
(5) Revolution: 3 rpm
(6) Distance of fall: 93 cm Further, the degree of discoloration of the stranded sample obtained by the high temperature processing of the styrene-butadiene block copolymer composition was visually evaluated and indicated by the following marks in Table 3.
O: No discoloration
Δ: Discoloration in light yellow
X : Discoloration in yellow

COMPARATIVE EXAMPLE 2:

Experiments were effected in the same manner as in the above Example 5 except that test compounds AO-1, AO-2, AO-3 and AO-4 were used in place of the compound II-1 or II-2 and the preventive effect of the test compounds against gelation and discoloration were evaluated. The results and loading amount of the test compounds are shown in Table 3.

TABLE 3

| Test Compound | | Example 5 | | | | Comparative Example 2 | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Loading amount | II-1 | 0.2 | 0.4 | | | | | | | | | | | None |
| | II-2 | | | 0.2 | 0.4 | | | | | | | | | |
| | AO-1 | | | | | 0.4 | 0.8 | | | | | | | |
| | AO-2 | | | | | | | 0.2 | 0.4 | | | | | |
| | AO-3 | | | | | | | | | 0.4 | 0.8 | | | |
| | AO-4 | | | | | | | | | | | 0.4 | 0.8 | |
| Gel content (%) | | 0.0 | 0.0 | 0.0 | 0.0 | 0.7 | 0.4 | 0.0 | 0.0 | 7 | 5 | 10 | 7 | 82 |
| Degree of discoloration | | O | O | O | O | Δ | X | O | O | O | Δ | O | O | X |

What is claimed is:

1. A phenolic compound represented by the formula:

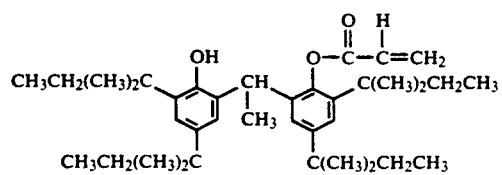

2. A phenolic compound represented by the formula:

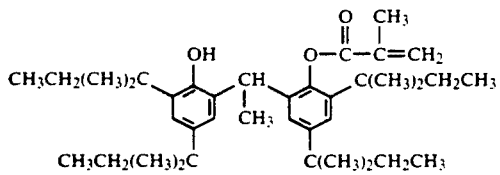

3. A stabilizer composition for a butadiene polymer comprising a stabilizingly effective amount of the phenolic compound of claim 1 and an inert carrier.

4. A stabilizer composition for a butadiene polymer comprising a stabilizingly effective amount of the phenolic compound of claim 2 and an inert carrier.

5. A stabilizer composition for a butadiene polymer comprising a stabilizingly effective amount of the phenolic compound of claim 1 which is dissolved in a hydrocarbon solvent.

6. A stabilizer composition for a butadiene polymer comprising a stabilizingly effective amount of the phenolic compound of claim 2 which is dissolved in a hydrocarbon solvent.

7. A stabilizer composition for a butadiene polymer comprising a stabilizingly effective amount of the phenolic compound of claim 1 and an additive selected from the group consisting of phenolic antioxidants, ultraviolet absorbers, hindered amine light stabilizers, sulfur-containing antioxidants and phosphorus-containing antioxidants.

8. A stabilizer composition for a butadiene polymer comprising a stabilizingly effective amount of the phenolic compound of claim 2 and an additive selected from the group consisting of phenolic antioxidants, ultraviolet absorbers, hindered amine light stabilizers, sulfur-containing antioxidants and phosphorus-containing antioxidants.

9. A method for stabilizing a butadiene polymer which comprises incorporating the phenolic compound of claim 1 into the butadiene polymer.

10. A method for stabilizing a butadiene polymer which comprises incorporating the phenolic compound of claim 2 into the butadiene polymer.

11. The method according to claim 9, wherein the butadiene polymer is prepared by anionic polymerization, and the phenolic compound is added to a polymerized reaction solution after the anionic polymerization is terminated.

12. The method according to claim 10, wherein the butadiene polymer is prepared by anionic polymerization, and the phenolic compound is added to a polymerized reaction solution after the anionic polymerization is terminated.

13. A butadiene polymer composition comprising a butadiene polymer and the phenolic compound of claim 1.

14. A butadiene polymer composition comprising a butadiene polymer and the phenolic compound of claim 2.

15. The butadiene polymer composition according to claim 13, wherein the butadiene polymer is solution polymerized polybutadiene rubber, solution polymerized styrene-butadiene copolymer rubber or styrene-butadiene block copolymer.

16. The butadiene polymer composition according to claim 14, wherein the butadiene polymer is solution polymerized polybutadiene rubber, solution polymerized styrene-butadiene copolymer rubber or styrene-butadiene block copolymer.

17. The butadiene polymer composition according to claim 13, wherein the phenolic compound is present in an amount of 0.05 to 2 parts by weight per 100 parts by weight of a butadiene polymer.

18. The butadiene polymer composition according to claim 14, wherein the phenolic compound is present in an amount of 0.05 to 2 parts by weight per 100 parts by weight of a butadiene polymer.

19. The butadiene polymer composition according to claim 17, wherein the amount of the phenolic compound is 0.1 to 1 part by weight per 100 parts by weight of the butadiene polymer.

20. The butadiene polymer composition according to claim 18, wherein the amount of phenolic compound is 0.1 to 1 part by weight per 100 parts by weight of the butadiene polymer.

* * * * *